United States Patent [19]

Beer

[11] 4,390,704

[45] Jun. 28, 1983

[54] PROCESS FOR THE PREPARATION OF 1,2,4-TRIAZOLE

[75] Inventor: Hans Beer, Vienna, Austria

[73] Assignee: Chemie Linz Aktiengesellschaft, Linz, Austria

[21] Appl. No.: 281,042

[22] Filed: Jul. 7, 1981

[30] Foreign Application Priority Data

Jul. 7, 1980 [AT] Austria ............................... 3533/80

[51] Int. Cl.³ .......................................... C07D 249/08
[52] U.S. Cl. .................................................. 548/262
[58] Field of Search ........................................ 548/262

[56] References Cited

U.S. PATENT DOCUMENTS 4,267,347  5/1981  Petree et al. ...................... 548/262

FOREIGN PATENT DOCUMENTS 3500   8/1979  Austria .
61617 12/1970  Luxembourg ...................... 548/262

OTHER PUBLICATIONS

Chemical Reviews-1961, p. 89.
J. Am. Chem. Soc., vol. 77, 1955, pp. 621–624.

Primary Examiner—Alton D. Rollins
Attorney, Agent, or Firm—Wenderoth, Lind & Ponack

[57] ABSTRACT

Preparation of 1,2,4-triazole by reacting formamide and hydrazine in a molar ratio of 2:1 to 2.2:1, hydrazine or its hydrate being metered into excess formamide, preheated to 160°–200°, while maintaining the temperature, and then completing the reaction at 160°–240° C.

8 Claims, No Drawings

PROCESS FOR THE PREPARATION OF 1,2,4-TRIAZOLE

The present invention relates to a process for the preparation of pure 1,2,4-triazole in a very good yield by reacting hydrazine with formamide at an elevated temperature in a molar ratio of formamide to hydrazine of 2:1 or greater.

1,2,4-Triazole derivatives have gained great importance as fungicides, medicaments and the like. Corresponding to the importance, numerous papers have been published which deal with the preparation thereof (see the summary in "Chemical Reviews" 1961, pages 88 et seq.).

For the preparation of the base material 1,2,4-triazole, formamide and hydrazine hydrate have already been used as raw materials at an early date. In spite of raising the temperature to 280° C., it was possible to achieve yields of only about 30% of theory when the process was carried out without applying pressure. With application of pressure, at a temperature of 200° C. and using excess ammonia, it was possible to increase the yield up to 70–80%, the reaction time being 24 hours (J. Am. Chem. Soc. Vol. 77, 1955, 621–624).

European patent application No. 3,500 has disclosed a process for the preparation of 1,2,4-triazole by reaction of hydrazine with formamide, wherein hydrazine is reacted with formamide in a molar ratio of 1:2.0 to 1:2.7 in the temperature range of 100° to 250° C. in the presence of ammonia, several reaction stages being operated at increasing reaction temperatures. The ammonia formed in the individual stages is here recycled into the preceding stages. This process gives yields of over 90% of theory, but it is very expensive since it requires a reaction cascade.

It has now been found, surprisingly, that pure 1,2,4-triazole can be produced readily and reliably in excellent yields in a one-stage reaction and without introduction of ammonia, when the reactants formamide and hydrazine are used, care is taken that excess preheated formamide is always available for the reaction with the hydrazine and the interaction of the two reactants takes place at a temperature of not less than 160° C. In this way, shorter reaction times are obtained; moreover, the proportion of by-products formed remains very small.

The process according to the invention for the preparation of 1,2,4-triazole by reacting hydrazine with formamide accordingly comprises operating in a single reaction stage with a molar ratio of formamide to hydrazine of 2:1 to 2.2:1, hydrazine as such or in the form of its hydrate being slowly metered into excess formamide preheated to a temperature in the range of 160° C. to 200° C. and the temperature being maintained within this range during metering-in, whereupon the reaction is subsequently completed at temperatures of 160°–240° C.

It is essential for the success of the reaction according to the invention that the formamide be laways present in excess over the hydrazine. It is therefore necessary to ensure that, during the introduction of the hydrazine, which is preferably used as hydrazine hydrate, the formamide is made up in good time, the temperature not being allowed to fall below 160° C. Preferably, the total quantity of formamide to be reacted is preheated at the outset and only then is the hydrazine or hydrazine hydrate introduced.

Advantageously, the temperature should be maintained between 165° and 190° C. during the introduction and during the subsequent reaction, a temperature range of 175°–185° C. being particularly preferred.

When carrying out th process according to the invention in practice, it has proved to be advantageous to proceed in such a way that the hydrazine is introduced, preferably injected through a jet, from a head vessel or by means of a pump into the initially introduced and preheated formamide, so that immediate good distribution results. Preferably, the hydrazine is metered in, near to the bottom of the heated formamide present in the reactor, under a slight elevated pressure which is sufficient to overcome the hydrostatic pressure applying at the entry point of the hydrazine, and is reacted there with the formamide. When an inlet tube is used, a sufficient elevated pressure above the hydrostatic pressure is an elevated pressure of about 0.1 bar. If jets are used for introducing the hydrazine, elevated pressures of 1–3 bars are generally advantageous for introducing the hydrazine, depending on the construction of the jet. It is also advantageous to stir during the reaction. The reaction starts quickly, and vapors of water and ammonia are evolved, which pass through the reaction mass. The reaction vessel advantageously carries a packed column which has the function of condensing entrained formamide and allowing water vapor and ammonia vapor to distill off. The more efficient the operation of this column, the less is it necessary to exceed the theoretical molar ratio, namely 2 mole parts of formamide to 1 mole part of hydrazine, in favor of the formamide.

After the total hydrazine required for the reaction has been introduced, in particular injected through a jet, the reaction mixture is advantageously stirred for a further half hour at the reaction temperature and, towards the end of the reaction, the temperature can be raised somewhat above the temperature of introduction. After the end of the reaction, the reaction mixture is advantageously cooled to about 140° C. and then to 130° C. Since the 1,2,4-triazole obtained as the reaction product would otherwise crystallise, because of its purity, it is advisable to remove it from the reactor at about 130° C., while it is still in the liquid state.

Amost theoretical yields are achieved in the process according to the invention. The crude triazole having a pale yellow color can be recrystallized from a suitable solvent, for example isopropyl alcohol, to give a readily crystallizing white product which shows a sharp melting point.

EXAMPLE

A reactor is used which consists of a stainless steel vessel having a capacity of about 200 l. The reactor is equipped with a 1 m long column, stirrer, thermometer and an injection tube which reaches down to almost the bottom of the vessel. During the reaction, hydrazine hydrate (about 64% strength hydrazine) is introduced through the injection tube. 60 kg of formamide are initially introduce and heated to an internal temperature of 180° C. In the course of about 4 hours, 30 kg of hydrazine hydrate are then metered in, whilst stirring, under a slightly elevated pressure in such a way that no hydrazine is entrained and the temperature can be maintained between 175° and 180° C. The rate of addition of the hydrazine depends on the efficiency of the column and of the descending condenser. After the addition of the hydrazine, the mixture is stirred for a further 30 minutes at 180° to 185° C. and is then cooled to about 140° C. The contents of the reactor are forced out, while still liquid, at about 130° to 140° C. and, after cooling, the product is comminuted using an appropriate device. In this way, 1,2,4-triazole is obtained which is colored only pale yellow and contains only small amounts of formamide. The yield is about 45 kg of 93% pure product, corresponding to a yield of 91% of theory.

I claim:

1. A process for the preparation of 1,2,4-triazole by reacting hydrazine and formamide, comprising mixing formamide with hydrazine in a molar ratio of formamide to hydrazine of 2:1 to 2.2:1 in such a way that hydrazine as such or in the form of its hydrate is introduced into the formamide, which formamide has been heated to a temperature of 160°-200° C., said reaction being carried out in such a way that formamide is always present in excess, maintaining the temperature of the reaction mixture in the range of 160°-200° C. while introducing the hydrazine or hydrate, and subsequently reacting the two reactants at a temperature of 160°-240° C. without an addition of ammonia from outside into the reaction zone.

2. A process as claimed in claim 1, wherein the total quantity of formamide is introduced initially.

3. A process as claimed in claim 1, wherein the temperature is maintained at 165°-190° C. during the addition of the hydrazine and during the reaction.

4. A process as claimed in claim 3, wherein the temperature is maintained at 175°-185° C.

5. A process as claimed in claim 1, wherein the hydrazine is introduced at the lowest possible level below the surface of the formamide under a pressure which is sufficient to overcome the hydrostatic pressure applying at the entry point of the hydrazine.

6. A process as claimed in claim 5, wherein the hydrazine is injected through a jet.

7. A process as claimed in claim 1, wherein the formamide entrained by the water vapor and ammonia, which have been formed during the reaction, is separated from these by condensation and is returned into the reaction.

8. A process as claimed in claim 1, wherein the mixture is stirred during the reaction.

* * * * *